United States Patent [19]

Okumoto et al.

[11] Patent Number: 5,686,479
[45] Date of Patent: Nov. 11, 1997

[54] IMMUNOSUPPRESSIVE DRUG

[75] Inventors: Takeki Okumoto; Kenji Chiba; Yukio Hoshino; Hirotsugu Komatsu; Mariko Nagasawa, all of Saitama; Hidekazu Aratani, Fukuoka; Michio Terasawa, Fukuoka; Minoru Moriwaki, Fukuoka, all of Japan

[73] Assignee: Yoshitomi Pharmaceutical Industries, Ltd., Osaka, Japan

[21] Appl. No.: 244,811

[22] PCT Filed: Dec. 10, 1992

[86] PCT No.: PCT/JP92/01619

§ 371 Date: Jun. 10, 1994

§ 102(e) Date: Jun. 10, 1994

[87] PCT Pub. No.: WO93/12117

PCT Pub. Date: Jun. 24, 1993

[30] Foreign Application Priority Data

| Dec. 11, 1991 | [JP] | Japan | 3-350889 |
| Jan. 14, 1992 | [JP] | Japan | 4-24848 |
| Feb. 4, 1992 | [JP] | Japan | 4-54382 |
| Apr. 21, 1992 | [JP] | Japan | 4-129455 |

[51] Int. Cl.$^6$ ................................................ A61K 31/41
[52] U.S. Cl. ................................................ 514/383
[58] Field of Search ......................... 514/410, 411, 514/383

[56] References Cited

U.S. PATENT DOCUMENTS

| 5,221,671 | 6/1993 | Okano et al. | 514/219 |
| 5,304,552 | 4/1994 | Okano | 514/219 |

FOREIGN PATENT DOCUMENTS

| 0368175 | 11/1989 | European Pat. Off. . |
| 0387613 | 3/1990 | European Pat. Off. . |
| 0367110 | 5/1990 | European Pat. Off. . |
| 0368175 | 5/1990 | European Pat. Off. . |
| 0387613 | 9/1990 | European Pat. Off. . |

OTHER PUBLICATIONS

Muiño et al, "Prolongation of Rabbit Skin Allograft Survival with Immunosuppression and Specific Antagonist of Platelet-Activating Factor", *Transplantation Proceedings*, vol. XX, No. 1 (Suppl. 1), pp. 313–315 (Feb. 1988).

Watanabe et al, "Stimulation of Neutrophil Adherence to Vascular Endothelial Cells by Histamine and Thrombin and Its Inhibitors by PAF Antagonist and Dexamethasone", *Br. J. Pharmacol.*, 102:239–245 (1991).

Walser et al, "Thienotriazolodiazepines as Platelet-Activating Factor Antagonists. Steric Limitations for the Substituent in Position 2", *J. Med. Chem.*, 34:1440–1446 (1991).

*Primary Examiner*—Joseph Conrad
*Attorney, Agent, or Firm*—Sughrue, Mion, Zinn, Macpeak & Seas

[57] ABSTRACT

An immunosuppressive drug, an autoimmune disease treating drug, an immunosuppression enhancing drug and a cell adhesion inhibitor, each containing a thienotriazolodiazepine compound wherein the 2-position of its diazepine ring is alkylated as an active ingredient, an immunosuppression method, an autoimmune disease treating method, an immunosuppression enhancing method and a cell adhesion inhibiting method, each of which comprising administering the compound, and uses of the compound for the production of an immunosuppressive drug, an autoimmune disease treating drug, an immunosuppression enhancing drug and a cell adhesion inhibitor.

5 Claims, 4 Drawing Sheets

IMMUNOSUPPRESSIVE DRUG

This application is a 371 of PCT/JP92/01619 filed Dec. 10, 1992.

[TECHNICAL FIELD]

This invention relates to an immunosuppressive drug which comprises a specific thienotriazolodiazepine compound, an immunosuppression method and use thereof.

[BACKGROUND ART]

Organ transplantation has been carried out extensively in recent years, with the use of immunosuppressive drugs such as ciclosporin, azathioprine, steroidal drugs and the like in order to inhibit rejection reactions caused by the transplantation. However, frequent use of these immunosuppressive drugs causes renal toxicity or other serious side effects, thus bringing about problems in the field of medical treatment.

It has been disclosed, for example, in *Transplantation Proceedings*, vol.20, no.2, supplement 1, pp.313–315 (February, 1988) that a platelet activating factor antagonist (PAF antagonist), which is expected to be used as a drug for the treatment of inflammatory diseases, allergic diseases and the like, is effective in increasing immunosuppression action of ciclosporin, and in Japanese Patent Application Toppyo No. Hei-3-500898 that side effects of ciclosporin are reduced by the combined use of a thienotriazolodiazepine.

Also, it has been revealed that intercellular adhesion molecules are taking an important role in rejection reactions at the time of organ transplantation. It has been reported that rejection reactions accompanying organ transplantation were suppressed with prolonged survival of the grafts when antibodies specific for LFA-1 (leukocyte function-associated antigen-1, a molecule composed of CD11a ($\alpha$ chain) and CD18 ($\beta$ chain)) and ICAM-1 (intercellular adhesion molecule-1), both known as intracellular adhesion molecules, were administered to mice which have been subjected to allogenic heart transplantation (*Science*, vol.225, pp.1125–1127, Feb. 28, 1992). In consequence, it is possible to suppress the organ transplantation-accompanying rejection reactions by the use of specific antibodies to inhibit the cell adhesion caused via the intercellular adhesion molecules LFA-1 and ICAM-1.

In addition, great concern has been directed in recent years toward the development of a method for the treatment of rheumatoid arthritis which is regarded as an considerable autoimmune disease because the disease is chronic by itself and progressive and entails joint function disorder. Though nonsteroidal anti-inflammatory drugs, steroidal drugs, immunomodulators and the like are used in the pharmacotherapy of articular rheumatism, it is necessary to develop more effective therapeutic drugs because nonsteroidal anti-inflammatory drugs are not so effective and steroidal drugs and immunomodulators generate side effects with a high frequency and sometimes result in serious cases. On the other hand, it has been reported that onset of arthritis was inhibited when an antibody specific for the intercellular adhesion molecule ICAM-1 was administered to a rat adjuvant arthritis model (*Journal of Immunology*, vol.147, pp.4167–4171, Dec. 15, 1991).

However, use of the antibody is limited because of a possibility to induce allergy, anaphylactic shock and the like when it is administered.

In consequence, it has been suggested that a drug which inhibits cell adhesion caused via the intercellular adhesion molecules LFA-1, ICAM-1 and the like, or a drug which inhibits expression of these intercellular adhesion molecules on the cell surface, could be used as an immunosuppressive drug having less side effects, because such a drug would inhibit organ transplantation-induced rejection reactions and would be useful for the treatment of autoimmune diseases.

DISCLOSURE OF THE INVENTION

With the aim of overcoming the aforementioned problems, the inventors of the present invention have conducted intensive studies and found that a thienotriazolodiazepine compound wherein the 2-position of its diazepine ring is alkylated can increase actions of ciclosporin and the like immunosuppressive drugs, shows an immunosuppression function by itself, has a function to inhibit adhesion of leukocytes to blood vessel endothelial cells and is possessed of an arthritis-depressing action, thus resulting in the accomplishment of the present invention.

Accordingly, the present invention provides an immunosuppressive drug, an autoimmune disease treating drug, an immunosuppression enhancing drug or a cell adhesion inhibitor, which contains a thienotriazolodiazepine compound wherein the 2-position of its diazepine ring is alkylated (to be referred to as "inventive compound" hereinafter in some cases) as an active ingredient, an immunosuppression method, an autoimmune disease treating method, an immunosuppression enhancing method or a cell adhesion inhibiting method, which comprises administering the inventive compound to mammals including human, and use of the inventive compound for the production of an immunosuppressive drug, an autoimmune disease treating drug, an immunosuppression enhancing drug or a cell adhesion inhibitor.

According to the inventive compound, the term alkyl means a straight or branched-chain alkyl having 1 to 6 carbon atoms, of which methyl is preferred.

Preferred examples of the inventive compound include 4-(2-chlorophenyl)-2-(2-(4-isobutylphenyl)ethyl)-6,9-dimethyl-6H-thieno[3,2-f][1,2,4]triazolo[4,3-a][1,4]diazepine (to be referred to as "compound A" hereinafter), 3-[4-(2-chlorophenyl)-6,9-dimethyl-6H-thieno[3,2-f][1,2,4]triazolo-[4,3-a][1,4]diazepin-2-yl]propionic acid morpholide (to be referred to as "compound B" hereinafter), optical isomers thereof (6S-(−) for instance), (+)-6-(2-chlorophenyl)-3-cyclopropanecarbonyl-8,11-dimethyl-2,3,4,5-tetrahydro-8H-pyrido[4',3':4,5]thieno[3,2-f][1,2,4]triazolo[4,3-a][1,4]-diazepine (to be referred to as "compound C" hereinafter), their pharmaceutically acceptable salts (hydrochloride, hydrobromate, maleate and the like) and hydrates (1 hydrate, ½hydrate, ⅔hydrate, 2 hydrate, 3 hydrate and the like), and these compounds are produced in accordance with the procedures disclosed in Japanese Patent Application Kokai Nos. Hei-1-156982, Hei-2-256681 and Hei-2-256682 which are incorporated herein by reference.

When the pharmaceutical preparation of the present invention is produced, it may contain the inventive compound preferably in a therapeutically effective amount, generally ranging from about 0.1 to 50 mg. The pharmaceutical preparation can be safely administered to patients orally or parenterally, by mixing the active ingredient with pharmaceutically acceptable carriers, fillers, diluents, solubilizing aids, disintegrating agents, binders and the like and making the resulting mixture into tablets, powders, capsules, injections, suppositories, intravenous drip infusions and the like. Its dose per day per adult may be in the range of generally from 5 to 100 mg for oral administration or from 1 to 50 mg for intravenous injection.

When used as an immunosuppression enhancing drug in combination with an immunosuppressive drug, it is preferable to administrate the inventive compound-containing pharmaceutical preparation and the immunosuppressive drug separately, and such a mode of administration is also included in the scope of the present invention as a matter of course. In that case, the immunosuppressive drug may have a known formulation, or a formulation modified by those skilled in the art within a proper range, and can be used in an amount ranging from 0.01 to 50 times weight of the inventive compound-containing pharmaceutical preparation. In this connection, when an organ transplantation is carried out, the inventive compound-containing pharmaceutical preparation to be used in the present invention may be administered to the donor prior to the organ transplantation or injected into the excised organ.

Examples of the immunosuppressive drugs include ciclosporin, azathioprine, steroid drugs, FK-506 (see EP-A 18416 for instance), ISP-I and its related compounds (WO 90/02727 and Japanese Patent Application Kokai No. Hei-3-128347) and the like.

When used as an articular rheumatism treating drug (antirheumatic drug), it may be used jointly with a nonsteroidal anti-inflammatory drug, a steroidal anti-inflammatory drug, an immunomodulator and the like.

The pharmaceutical preparation of the present invention is used for the purpose of inhibiting rejection reactions which occur at the time of organ or bone marrow transplantation, or with the aim of preventing or treating autoimmune diseases such as articular rheumatism, systemic lupus erythematosus, Sjoegren syndrome, multiple sclerosis, myasthenia gravis, type I diabetes mellitus, endocrine ophthalmic disease, primary biliary cirrhosis, Crohn disease, glomerular nephritis, sarcoidosis, psoriasis, variola, hypoplastic anemia, idiopathic thrombocytopenic purpura and the like.

[BRIEF DESCRIPTION OF THE DRAWINGS]

FIG. 1 shows a case in which full-thickness skin grafts of WKAHmale rats of 4 weeks of age were transplanted by suture to the lateral thorax of F344 male rats of 4 weeks of age, but not treated with a sample to be tested, FIG. 2 is a case in which 3 mg/kg of ciclosporin (shown as CsA) was intraperitoneally administered once a day to the same experimental model rats and FIG. 3 is a case in which 3 mg/kg of ciclosporin was intraperitoneally administered once a day, while simultaneously carrying out oral administration of 10 mg/kg of compound A (shown as Y-24180) once a day.

[BEST MODE OF CARRYING OUT THE INVENTION]

Figure 1:
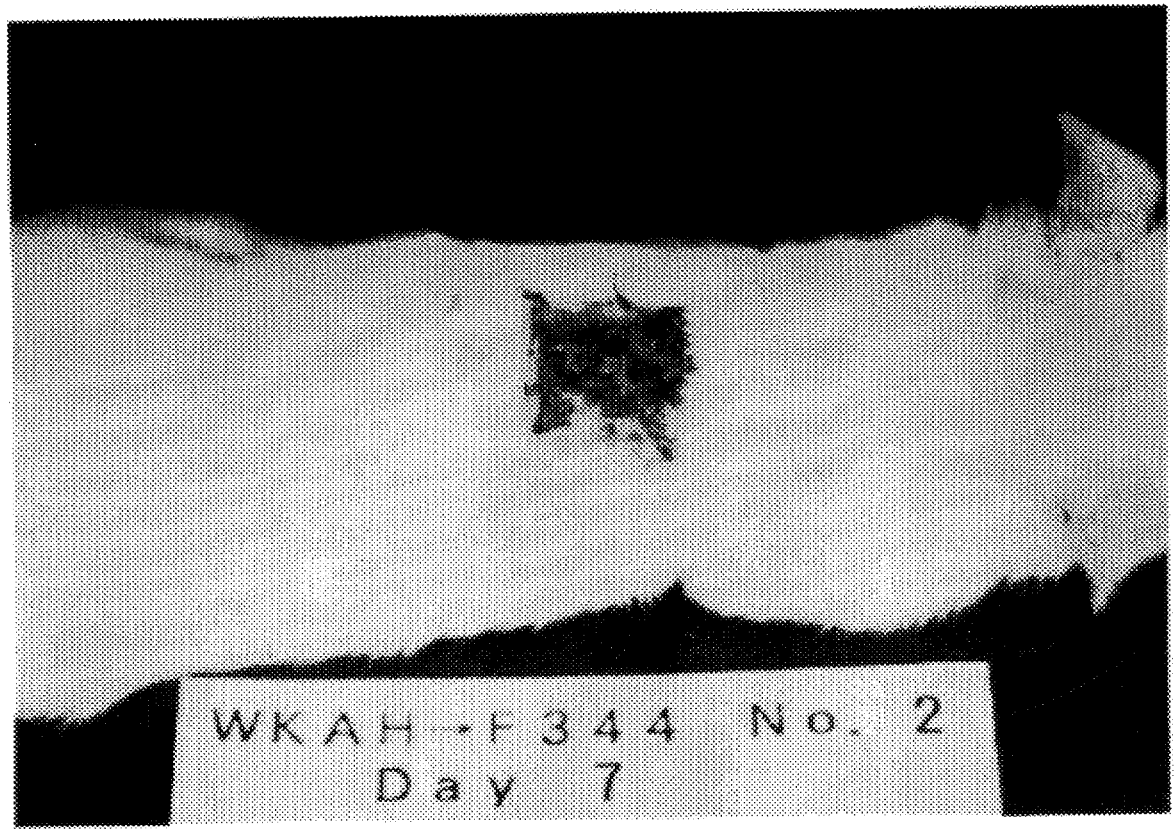
FIGS. 1 to 3 are photographs showing conditions of skin grafts observed at the 7th day after skin transplantation experiments of rats with no treatment, administered with 3 mg/kg of ciclosporin (CsA) or administered with 10 mg/kg of compound A (shown as Y-24180) and 3 mg/kg of ciclosporin. That is.
Figure 2:
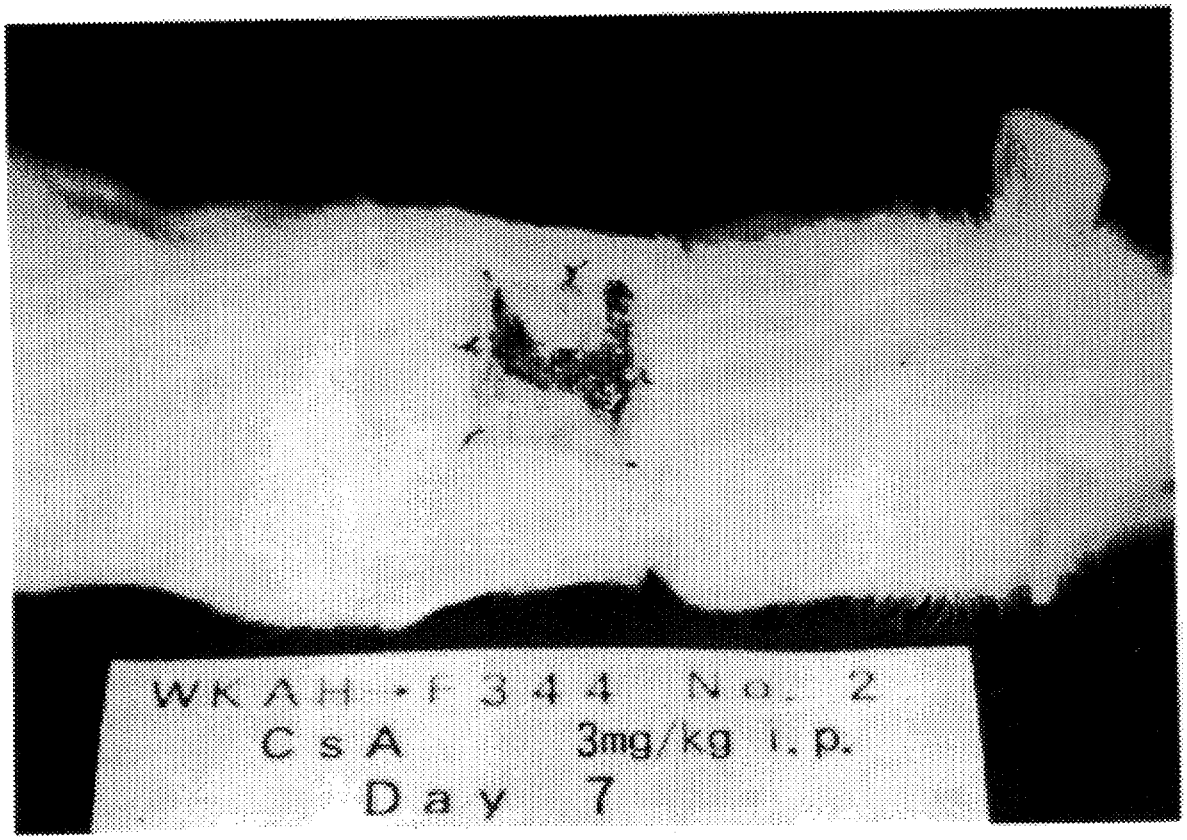
Figure 3:
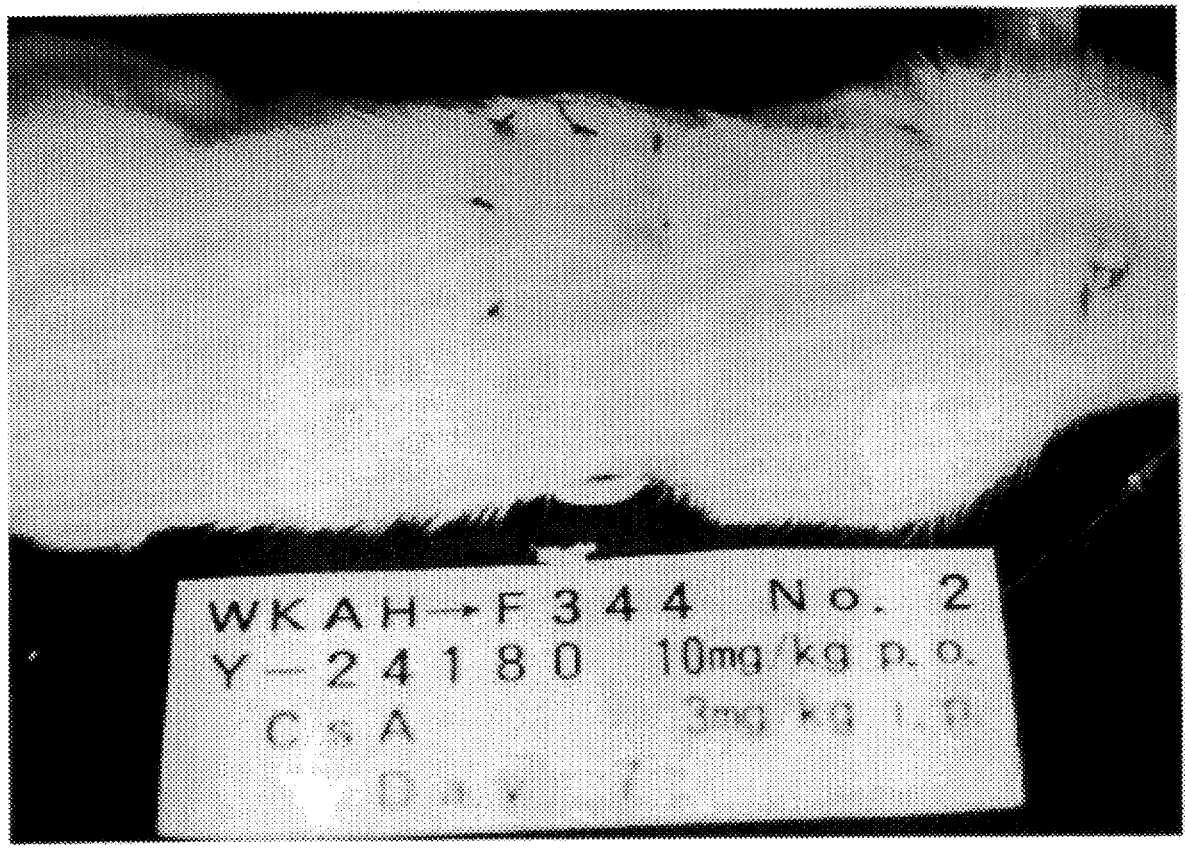

The following formulation and experimental examples are provided to further illustrate the present invention, but not by way of limitation.

FORMULATION EXAMPLE 1

(1) Ciclosporin Oral Preparation (Trade Name, Sandimmun Oral Preparation)

(2) Tablets Containing 0.5 mg of Compound A

A 0.5 part of compound A was thoroughly mixed with 25 parts of lactose, 35 parts of crystalline cellulose and 3 parts of corn starch, and the mixture was kneaded thoroughly with a binder made of 2 parts of corn starch. The thus kneaded product was filtered through a 16 mesh screen, dried at 50° C. in an oven and then filtered through a 24 mesh screen. The thus obtained powder was thoroughly mixed with 8 parts of corn starch, 11 parts of crystalline cellulose and 9 parts of talc, and the mixture was compression-tabletted to obtain tablets each containing 0.5 mg of the active ingredient.

Each of these preparations is administered to patients continuously or intermittently before and/or after an organ or bone marrow transplantation operation.

FORMULATION EXAMPLE 2

(1) Ciclosporin Injection (Trade Name, Sandimmun Injection)

(2) Injection Containing 1 mg of Compound B

This preparation is produced by dissolving 1.0 mg of compound B and 9.0 mg of sodium chloride in distilled water for injection use, removing pyrogen by filtration, putting the resulting filtrate into an ampul under aseptic condition, sterilizing the filtrate included in the ampul and then sealing the ampul by melting.

Each of these preparations is administered to patients continuously or intermittently before and/or after an organ or bone marrow transplantation operation.

FORMULATION EXAMPLE 3

A 0.5 part of compound A was thoroughly mixed with 25 parts of lactose, 35 parts of crystalline cellulose and 3 parts of corn starch, and the mixture was kneaded thoroughly with a binder made of 2 parts of corn starch. The thus kneaded product was filtered through a 16 mesh screen, dried at 50° C. in an oven and then filtered through a 24 mesh screen. The thus obtained powder was thoroughly mixed with 8 parts of corn starch, 11 parts of crystalline cellulose and 9 parts of talc, and the mixture was compression-tabletted to obtain tablets each containing 0.5 mg of the active ingredient.

FORMULATION EXAMPLE 4

An injection preparation containing 1.0 mg of active ingredient is obtained by dissolving 1.0 mg of compound A and 9.0 mg of sodium chloride in distilled water for injection use, removing pyrogen by filtration, putting the resulting filtrate into an ampul under aseptic condition, sterilizing the filtrate included in the ampul and then sealing the ampul by melting.

EXPERIMENTAL EXAMPLE 1

The Potentiating Effect of the Graft Survival Prolongation by the Combination of Ciclosporin on Rat Allogeneic Skin Transplantation The rat allogeneic skin transplantation was carried out as following methods.

Full-thickness skin grafts (2×2 cm) from four weeks old male WKAH rats (five rats per group) were transplanted to the lateral thorax of four weeks old male F344 rats by suture, covered with sterile gauze and wrapped with bandages. The dressings were removed on day 6, and the grafts were inspected daily until rejectiota. Rejection was defined as more than 90% brown necrosis of the graft epithelium. Graft survival day was designated periods of the day from transplantation to rejection.

Test compounds were suspended in a 0.5% methylcellulose solution and administered orally once a day from allografting until rejection.

Intravenous formulation of ciclosporin was diluted with physiological saline and intraperitoneally administered once a day for 10 days until the 9th postoperative day.

The mean survival time was calculated base on the graft survival day of each rat. The results were shown as Tables 1 to 3.

TABLE 1

| Doner | Recipient | Test Sample | Dose (mg/kg) | Mean graft survival (day ± S.D.) |
|---|---|---|---|---|
| WKAH | F344 | — | — | 6.4 ± 0.5 |
| WKAH | F344 | Compound A | 10 | 6.8 ± 0.4 |
| WKAH | F344 | Ciclosporin | 3 | 8.2 ± 0.4 |
| WKAH | F344 | Compound A | 10 | 10.2 ± 0.8** |
| | | + | | |
| | | Ciclosporin | 3 | |
| WKAH | F344 | Compound B | 10 | 9.2 ± 0.4* |
| | | + | | |
| | | Ciclosporin | 3 | |
| WKAH | F344 | Compound C | 10 | 9.6 ± 0.5* |
| | | + | | |
| | | Ciclosporin | 3 | |

(The symbols * and ** mean statistically significant at $p < 0.05$ and $p < 0.01$, respectively compared with control group using the Mann-Whitney U-test.)

As shown in Table 1, it is clear that the combination of Ciclosporin and compound A, compound B or compound C prolonged the graft survival day significantly.

TABLE 2

| Doner | Recipient | Test Sample | Dose (mg/kg) | Mean graft survival (day ± S.D.) |
|---|---|---|---|---|
| WKAH | F344 | — | — | 6.2 ± 0.4 |
| WKAH | F344 | Ciclosporin | 3 | 8.2 ± 0.4 |
| WKAH | F344 | Compound A | 0.3 | 9.6 ± 0.9** |
| | | + | | |
| | | Ciclosporin | 3 | |
| WKAH | F344 | Compound A | 1 | 10.0 ± 0.7** |
| | | + | | |
| | | Ciclosporin | 3 | |
| WKAH | F344 | Compound A | 3 | 10.2 ± 0.8** |
| | | + | | |
| | | Ciclosporin | 3 | |
| WKAH | F344 | Compound A | 10 | 10.2 ± 0.8** |
| | | + | | |
| | | Ciclosporin | 3 | |

(The symbol ** mean statistically significant at $p < 0.01$, compared with control group using of Mann-Whitney U-test.)

As shown in Table 2, it is clear that compound A prolong the graft survival day in dose-dependently and significantly as compared with Ciclosporin-administered group.

TABLE 3

| Doner | Recipient | Test Sample | Dose (mg/kg) | Mean graft survival (day ± S.D.) |
|---|---|---|---|---|
| WKAH | F344 | — | — | 6.4 ± 0.5 |
| WKAH | F344 | Ciclosporin | 10 | 10.8 ± 0.8 |
| WKAH | F344 | Ciclosporin | 30 | 14.4 ± 0.5 |
| WKAH | F344 | Compound A | 10 | 13.4 ± 0.5** |
| | | + | | |
| | | Ciclosporin | 10 | |
| WKAH | F344 | Compound A | 10 | 18.8 ± 1.6** |
| | | + | | |
| | | Ciclosporin | 30 | |

(The symbol ** means statistically significant at $p < 0.01$, compared with control group using of Mann-Whitney U-test.)

As shown in Table 3, it is clear that compound A prolong the graft survival day significantly versus high does of Ciclosporin-treated groups.

EXPERIMENTAL EXAMPLE 2

Inhibitory Effect on Adhesion of U937 Cells (Human Histiocytic Leukemia Cells) to Human Umbilical Vein-derived Endothelial Cells (HUVSCs)

HUVECs were suspended in 199 medium supplemented with fetal calf serum (20%), endothelial cell growth factor derived from bovine brain (20 µg/ml) and heparin (100 µg/ml). Cells were plated into 96-well culture plates coated with collagen and cultured at 37° C. in the presence of 5% $C_2$. When cells were grown to confluence, interleukin-1 (10 U/ml) was added to the cells and the plates were incubated for additional 24 hour. After the plates were washed, leukotrien $B_{/4}$ (1 µM), compound A as a test compound and U937 cells ($3 \times 10^5$ cells/well) were added to the wells, then the plates were incubated for 30 minutes. After non-adherent cells were removed by inversion of the plates, Rose bengal solution (0.25% in phosphate-buffered saline) was added to the cells. After incubation for 5 minutes, the plates were washed twice with 199 medium to remove non-adherent cells. Rose bengal dye incorporated into cells was extracted by incubation with 50% ethanol in phosphate-buffered saline for 20 minutes. Absorbance at a wavelength of 570 nm was measured with a 96-well plate reader and the value obtained by subtracting the absorbance of wells of HUVECs alone from that of HUVECs plus U937 cells was defined as adhesion of U937 cells.

Result was shown in Table 4.

TABLE 4

| Leukotrien $B_4$ (µM) | Compound A (µM) | U937 cell adhesion (absorbance at 570 nm) | Inhibition (%) |
|---|---|---|---|
| 0 | 0 | 0.143 | 100 |
| 1 | 0 | 0.449 | 0 |
| 1 | 0.1 | 0.451 | −0.7 |
| 1 | 1 | 0.404 | 14.7 |
| 1 | 10 | 0.199 | 81.6 |

As shown in Table 4, compound A inhibited adhesion of U937 cells to HUVECs in a dose-dependent manner and the $IC_{50}$ value was about 3 µM.

EXPERIMENTAL EXAMPLE 3

Effect on CD18 Expression on Human Peripheral Blood Neutrophils

Effect on expression of CD18 molecule was examined; CD18 molecule is composing a β chain of LFA-1 which is one of adhesion molecules expressing on the surface of almost all of leukocytic cells.

Human peripheral blood neutrophils prepared with dextran were suspended in RPMI1640 medium containing fetal calf serum (20%) and added into 96-well filtration plates ($2\times10^5$ cells/well) with leukotrien $B_4$ (1 µM) and compound A as a test compound. After incubated for 90 minutes at 37° C. in the presence of 5% $CO_2$, cells were washed once with RPMI1640 medium and treated with mouse anti-human CD18 monoclonal antibody (4 µg/ml) for 1 hour on ice. After washed once, cells were treated with peroxidase-conjugated anti-mouse immunoglobulin antibody (2.5 µg/ml) for 1 hour on ice. After cells were washed twice, substrate for peroxidase (2,2'-azino-bis(3-ethylbenzothiazoline-6-sulfonic acid)) was added to the cells and the plates were incubated for 30 minutes at room temperature. Absorbance at a wavelength of 405 nm was measured with a 96-well plate reader and taken as an indicator of CD18 expression.

Result was shown in Table 5.

TABLE 5

| Leukotrien $B_4$ (µM) | Compound A (µM) | CD18 expression (absorbance at 405 nm) | Inhibition (%) |
| --- | --- | --- | --- |
| 0 | 0 | 0.100 | 100 |
| 1 | 0 | 0.156 | 0 |
| 1 | 0.1 | 0.143 | 23.8 |
| 1 | 1 | 0.134 | 39.9 |
| 1 | 10 | 0.108 | 85.1 |

As shown in Table 5, compound A inhibited CD18 expression on human peripheral blood neutrophils in a dose-dependent manner and the $IC_{50}$ value was about 2 µM.

EXPERIMENTAL EXAMPLE 4

Effect on Oxazolone-induced Ear Edema in Mice

Mice were sensitized by applying 50 µl of oxazolone solution (50 mg/ml in acetone) to shaved abdomen. On the 6th day after the sensitization, 5 µl of oxazolone solution was applied to each of inside and outside of the right ear. After 24 hour, the right and left ears were cut off with a puncher (6 mm in diameter) and weighed with an electric reading balance. The difference in weight between the treated (right) and untreated (left) ears was taken to reflect the extent of ear edema. Compound A as a test compound was suspended in a 0.5% methylcellulose solution and administered orally (0.1 ml/10 g of body weight) on the 3rd, 4th, 5th and 6th days after the sensitization.

Result was shown in Table 6.

TABLE 6

| Treatment | Compound A (mg/kg/day) | Ear edema (right ear - left ear) (mg, mean ± S.D.) |
| --- | --- | --- |
| Unsensitized | 0 | 1.5 ± 1.3 |
| Sensitized | 0 | 12.9 ± 2.4 |
| Sensitized | 3 | 10.3 ± 4.3 |
| Sensitized | 10 | 10.0 ± 1.6* |
| Sensitized | 30 | 8.2 ± 1.0** |
| Sensitized | 100 | 7.7 ± 2.3** |

(The symbol * and ** means statistically significant at p < 0.05 and p < 0.01, respectively compared with control group using Mann-Whitney's U-test.)

As shown in Table 6, Compound A inhibited ear edema in mice dose-dependently. This data suggests that this compound suppresses leukocyte infiltration into inflammatory sites by inhibiting leukocyte adhesion in vivo and is effective on rheumatoid arthritis.

EXPERIMENTAL EXAMPLE 5

Effect on Collagen-induced Arthritis in Rats

Male Sprague Dawley rats (body weight: about 200 g, Charles River Japan, Inc.) were utilized. Preparation of Type II collagen was performed according to the method of Trentham et al. (J. Exp. Med., 146, 857–868, 1977). One ml of a collagen emulsion containing 1 mg of collagen (collagen was dissolved at 2 ml/kg in a 0.1N acetic acid and mixed with equal volume of Freund incomplete adjuvant, thereby the emulsion was prepared) was injected intradermally at the 5 points on the shaved back of ether-anesthetized rats (7 heads/group). Seven days later, 0.2 ml of the emulsion described above was injected intradermally at the root of tail. Compound A as a test compound was administered orally from the day of collagen sensitization to day 21 (once daily, 5 ml/1 kg body weight). Foot volume was measured with a digital volume meter (Muromachi Kikai Co., Ltd.). In addition, blood was gathered from vein of fundus oculi. Level of anti-type II collagen antibody in the blood was determined by enzyme-linked immunosorbent assay (absorbance at 405 nm was measured) and percent inhibition of antibody production was calculated. The results were shown in Table 7.

TABLE 7

| | | Level of anti-type II collagen antibody | |
| --- | --- | --- | --- |
| Test compound | Dose (mg/kg, p.o) | Mean ± S.D. | Inhibition (%) |
| Control | 0 | 0.824 ± 0.044 | — |
| Compound A | 3 | 0.856 ± 0.055 | -3.9 |
| Compound A | 10 | 0.658 ± 0.129 | 20.4 |
| Indomethacin | 0.3 | 0.889 ± 0.051 | -8.0 |
| Indomethacin | 1 | 0.674 ± 0.112 | 18.5 |
| Compound A + Indomethacin | 3 0.3 | 0.564 ± 0.085* | 32.0 |
| Compound A + Indomethacin | 3 1 | 0.443 ± 0.120** | 46.5 |

(The symbol * and ** mean statistically significant at p < 0.05 and p < 0.01, respectively compared with control group using the Mann-Whitney's U-test.)

Arthritis occurred on the 10th day after collagen sensitization. Consecutive administration of Compound A for 21 days (3 and 10 mg/kg) significantly inhibited arthritis in a dose-dependent manner and the effect lasted after completion of administration. Although oral administration of indomethacin at 0.3 and 1 mg/kg significantly inhibited in a dose-dependent manner, the inhibited arthritis revived after completion of administration. In combined administration of Compound A and indomethacin, the effect was stronger than that in administration of each drug. Oral administration of Compound A (10 mg/kg) or indomethacin (1 mg/kg) induced a tendency to inhibit production of anti-type II collagen antibody. Significant inhibition of antibody production was observed in combination of both drugs.

EXPERIMENTAL EXAMPLE 6

Effect on Collagen-induced Arthritis in Mice

Male DBA/1J mice (8 weeks of age, Seiwa Experimental Animals, Ltd.) were utilized. Collagen emulsion (0.1 ml)

prepared as described in Experimental Example 5 was injected intradermally at the root of tail of ether-anesthetized mice (10 heads/group). Twenty one days later, mice were additionally immunized by the same procedure. Test compound was administered orally on consecutive days for 10 weeks beginning on the day of collagen sensitization (once daily, 10 ml/1 kg body weight). Arthritis of the limbs 4 was scored according to the following categories:

0 point: no arthritis; 1 point: 2 or less finger with swelling; 2 point: 3 or more finger with swelling; 3 point: mild edema; 4 point: moderate edema; 5 point: severe edema.

Figure 4:
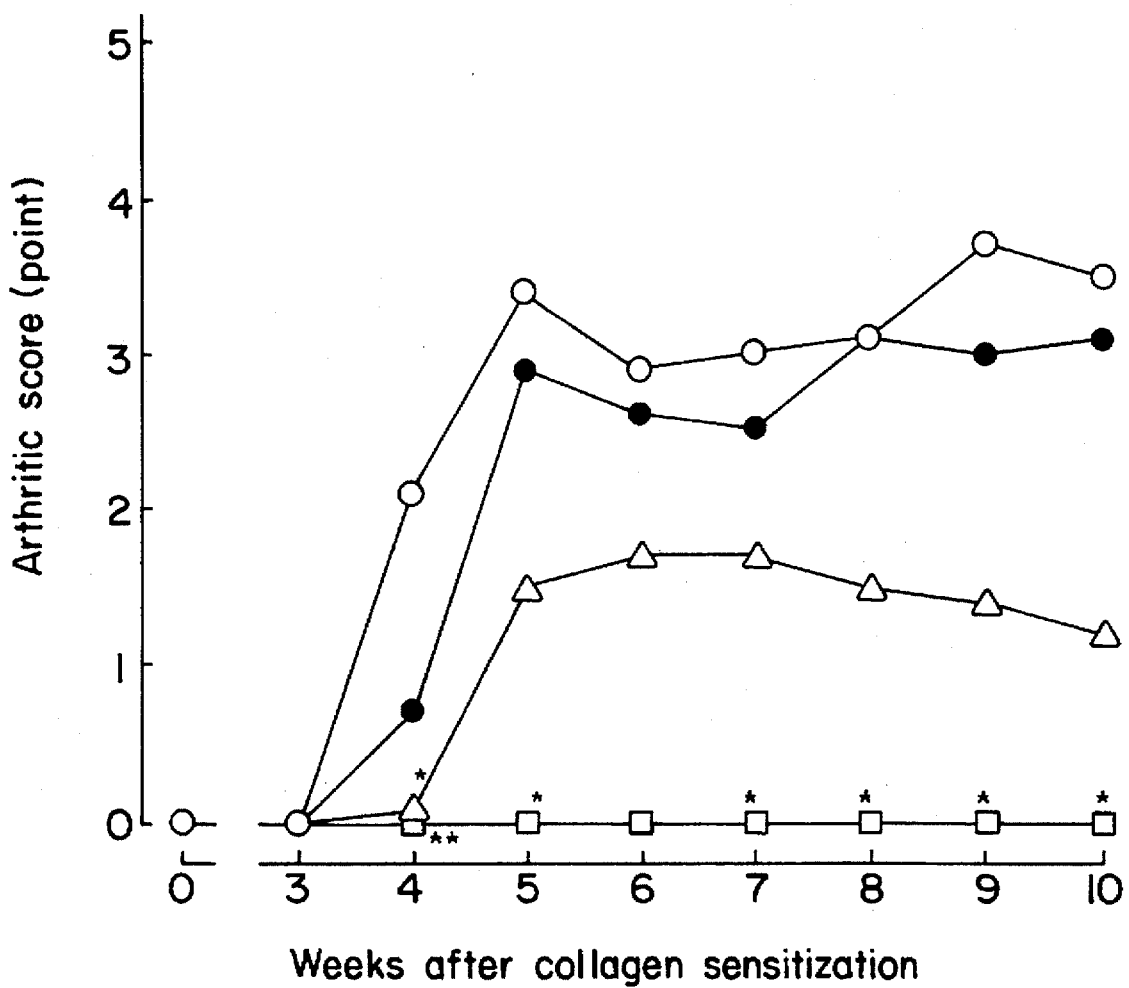
FIG. 4 is a graph showing effects of the action of compounds on collagen-induced arthritis in mice. In the drawing, -O-O- represent a control group, -●-●- represent a group orally administered with 3 mg/kg of compound A, -△-△- represent a group orally administered with 10 mg/kg of compound A and -□-□- represent a group orally administered with 10 mg/kg of hydrocortisone.

The result was shown in FIG. 4.

Arthritis occurred at the 4 weeks after collagen sensitization. Oral administration of compound A at 3 and 10 mg/kg significantly inhibited arthritis in a dose-dependent manner. Arthritis was not observed in the mice to which hydrocortisone at 10 mg/kg was orally administered.

[INDUSTRIAL APPLICABILITY]

As is evident from the description including the above Experimental Examples, the inventive compound is useful as an immunosuppressive drug, an immunosuppression enhancing drug, an autoimmune disease treating drug or a cell adhesion inhibitor, because it increases the action of immunosuppressive drugs such as ciclosporin and the like, shows immunosuppression function by itself and has cell adhesion inhibition activity.

Though the present invention has been illustratively described by the specification including formulation examples and various experimental examples, it may be altered and modified in various ways without departing from the spirit and scope of the invention.

We claim:

1. A method for inhibiting cell adhesion, wherein said cell adhesion is caused by intercellular adhesion molecules, which comprises the step of administering to a subject in need of such inhibiting an effective amount of 4-(2-chlorophenyl)-2-(2-(4-isobutylphenyl)-ethyl)-6,9-dimethyl-6H-thieno [3,2-f][1,2,4]triazolo[4,3-a][1,4]diazepine, an optical isomer thereof, or a pharmaceutically acceptable acid addition salt or hydrate thereof.

2. The method of claim 1, wherein the effective amount of 4-(2-chlorophenyl)-2-(2-(4-isobutylphenyl)-ethyl)-6,9-dimethyl-6H-thieno[3,2-f][1,2,4]triazolo[4,3-a][1,4] diazepine ranges from about 0.1 to 50 mg.

3. A method for inhibiting expression of intercellular adhesion molecules which comprises the step of administering to a subject in need of such inhibiting an effective amount of 4-(2-chlorophenyl)-2-(2-(4-isobutylphenyl)-ethyl)-6,9-dimethyl-6H-thieno[3,2-f][1,2,4]triazolo[4,3-a][1,4]diazepine, an optical isomer thereof, or a pharmaceutically acceptable acid addition salt or hydrate thereof.

4. The method according to claim 3, wherein the effective amount of 4-(2-chlorophenyl)-2-(2-(4-isobutylphenyl)-ethyl)-6,9-dimethyl-6H-thieno[3,2-f][1,2,4]triazolo[4,3-a][1,4]diazepine ranges from about 0.1 to 50 mg.

5. A method for inhibiting at least one of the intercellular adhesion molecules $LB_4$ or $CD_{18}$, which comprises the step of administering to a subject in need of such inhibiting an effective amount of 4-(2-chlorophenyl)-2-(2-(4-isobutylphenyl)-ethyl)-6,9-dimethyl-6H-thieno[3,2-f][1,2,4]triazolo[4,3-a][1,4]diazepine, an optical isomer thereof, or a pharmaceutically acceptable acid addition salt or hydrate thereof.

* * * * *